United States Patent [19]

Paterson et al.

[11] Patent Number: 4,687,743
[45] Date of Patent: Aug. 18, 1987

[54] SUNFLOWER REGENERATION MEDIA, METHOD OF USE AND PLANTS REGENERATED THEREON

[75] Inventors: Karol E. Paterson, Oakland; Nicholas P. Everett, El Sobrante, both of Calif.

[73] Assignee: Stauffer Chemical Company, Richmond, Calif.

[21] Appl. No.: 584,079

[22] Filed: Feb. 27, 1984

[51] Int. Cl.$^4$ .......................... C12N 5/00; C12N 5/02
[52] U.S. Cl. ............................ 435/240.49; 435/240.54
[58] Field of Search ..................... 435/240, 241; 800/1

[56] References Cited

U.S. PATENT DOCUMENTS 4,552,844 11/1985 Everett ................................ 435/240

FOREIGN PATENT DOCUMENTS 0132360 1/1985 European Pat. Off. ............ 435/240

OTHER PUBLICATIONS

Paterson 1984, "Shoot Tip Culture of *Helianthus Annuus*-Flowering and Development . . . "Am. J. Bot. V71, 925–31.

Georgieva-Todordva 1980 Proc. 9th Int'l. Sunflower Conference Torremolinos, Spain.

Conger (Ed) 1981 *Cloning Agricultural Plants Via In Vitro Techniques* CRC Press, Inc. Boca Raton, pp. 13, 47, 56, 195–196, 211.

Dodds (Ed) 1982 *Experiments in Plant Tissue Culture*, Chapter 7, "Organogenesis" pp. 78–88.

*Primary Examiner*—Thomas G. Wiseman
*Assistant Examiner*—David T. Fox
*Attorney, Agent, or Firm*—Michael J. Bradley; Jacqueline S. Larson

[57] ABSTRACT

Sunflower regeneration media comprising minimal salts, a carbohydrate source, and regeneration-effective mixtures of plant hormones and regeneration-effective mixtures of vitamins are disclosed and claimed. A method of screening sunflower seedlines for regeneration using the medium is disclosed and claimed. A method for regenerating sunflower plants using the medium is also disclosed.

21 Claims, No Drawings

SUNFLOWER REGENERATION MEDIA, METHOD OF USE AND PLANTS REGENERATED THEREON

FIELD OF THE INVENTION

The instant invention concerns the regeneration of sunflower plants from cultured sunflower tissue. In particular, the invention concerns a medium for selecting sunflower seed lines that can regenerate sunflower plants from sunflower callus. Furthermore, the invention relates to a method for selecting sunflower seed lines that can regenerate sunflower plants from sunflower callus.

BACKGROUND OF THE INVENTION

Vegetative propagation of agriculturally important plant species is a well known and valuable practice in some fields of agriculture. In the horticultural arts for example, ornamental flowers are vegetatively propagated from callus. Callus may be defined as a collection of plant cells that have become dedifferentiated usually under the influence of plant hormones such as auxins, for example indole acetic acid (IAA) and auxin-like compounds, for example 2,4-dichloro phenoxyacetic acid (2,4-D). Cellular division of such differentiated plant cells usually produces poorly organized cells that may be further propagated in a growth medium, provided that an auxin or auxin-like plant hormone is present in the growth medium. By adjusting nutrient, vitamin, and plant hormones levels, plants that are essentially identical to the individual plant from which the callus was initiated can be regenerated. For example, using these general methods, the production of thousands of identical orchids is routinely possible from the somatic cells of a single orchid plant.

Vegetative propagation of crop plants by inducing callus, maintaining the callus and regenerating plants from the callus has great potential in the development and improvement of food crops. For example, vegetative propagation may be used to multiply inbred or hybrid plant strains that have commercially valuable or scientifically interesting characteristics which occur rarely or are unstable when the plant reproduces sexually. Tissue obtained from such scientifically interesting or commercially valuable plants can be used to propagate numerous copies of the original plant, thereby stably maintaining the otherwise unstable characteristics.

Callus induced from the tissue of a unique or valuable plant can be multiplied and plants can be regenerated from the callus. Thus multiple copies of a single unique or valuable plant can be reproduced for further breeding, genetic selection or genetic manipulation using recombinent nucleic acid techniques. Plants having unique traits can thus be used in breeding programs without risk of losing the desirable characteristics that may be unstable.

Sunflower (*Helianthus annuus*, hereinafter referred to as *H. annuus*), is one of four major crops grown for edible oil. Ninety percent of the sunflower crop grown in the United States is used for oil production. Development of a system that permits oil-producing inbreds of *H. annuus* to regenerate plants from tissue or callus culture would be useful as a supplement to current plant breeding programs.

Most reports on tissue culture of *H. annuus* have concerned crown gall cells, i.e. plant tumor cells produced as a result of infection by the bacterial plant pathogen *Agarobacterium tumafaciens*, but there has been some work on callus production from normal sunflower tissues (see for example, Kandler, O., *Planta*, Bd. 40: 346–349 (1952); Henderson et al., *Amer. J. Bot.* 39: 467–473 (1955); Rogers et al., In Vitro 9: 462–467 (1974). In addition, there have been three reports of plant or shoot regeneration from cultured sunflower tissue. M. K. Sadhu reported plant regeneration from sunflower stem pith cultured on a modified White's medium with 1 part per million (ppm) IAA (see Sadhu, M. K., *Indian J. Exp. Biol.*, 12: 110–111 (1979)). Binding et al. reported shoot regenertion from protoplasts isolated from cultured shoot tips, although no details were presented (Binding et al. *Z Planzenphysiol-Bd.* 101: 119–130 (1981)). In these two reports, no information was presented regarding the seed source. The source could have been confectionary (non-oil-producing) hybrids or open pollinated varieties. Georgieva-Todorova et al. reported callus induction and shoot regeneration from two sterile hybrids—*H. annus*×*H. decapetalus* and *H. annus*×*H. hirsutus* (Georgieva-Todordva, et al. *Proc. 9th Int'l Sunflower Conf.* Torremolinos Spain (1980)).

Georgieva-Todorova et al. specifically disclose a medium that allows sunflower callus growth and organogenic regeneration of sunflower shoots from tissue of sterile hybrid sunflower plants. The medium disclosed by Georgieva-Todorova (GT medium) is composed of a range of plant hormones, White's vitamins, and major and minor salts disclosed in Murashige, T. and Skoog, F., (1962) *Physiologia Plantarium*, 15: 443–97. The vitamins disclosed in GT medium are as follows:

| Vitamin Component | Concentration (per 1 medium) |
|---|---|
| thiamine.HCl | 0.1 mg |
| nicotinic acid | 0.5 mg |
| pyridoxine.HCl | 0.5 mg |
| Ca—pantothenate | 1.0 mg |
| inositol | 500.0 mg |
| glycine | 3.0 mg |
| adenine sulfate | 40.0 mg |
| cysteine | 1.0 mg |

The plant hormones disclosed by Georgieva-Todorova et al. are numerous and depending upon the particular mix of hormones and concentration of the particular hormone used in the mix various results are obtained. Thus quick growth of callus with rapid differentiation of meritematic centers is observed in the GT media described above having 0.1 or 10 mg/l benzylamino purine (benzyladenine hereinafter referred to as BA); 0.1 or 10 mg/l indolbutryic acid (hereinafter IBA); 0.1 mg/l BA with 0.1 or 10 mg/l naphthalene acetic acid (NAA); and a combination of 10.0 mg/l BA with 0.1 or 10 mg/l NAA.

Specifically, the best organogenesis was observed in GT medium composed of MS salts and vitamins as described above and the plant hormones as follows: 0.1–0.5 mg/l NAA, 0.1 mg/l BA, and 0.01 mg/l gibberllic acid (GA). The best organogenesis occurred with this mix of plant hormones when the NAA concentration was 0.1 mg/l.

The experiments of Georgieva-Todovova et al. disclose several plant hormone concentrations that appear to permit significant regeneration of sunflower tissue in two sterile hybrid sunflower seed lines. As will be seen below Georgieva-Todorova et al. do not, however, disclose media that may be used to regenerate sunflower tissue from inbred sunflower seed lines. The value of the regeneration medium disclosed by Georgieva-Todovova et al. is thus limited, since the sunflower seed lines to which it has been successfully applied are sterile hybrid seed lines that cannot be used for breeding or genetic selection purposes.

One of the problems facing workers seeking to regenerate sunflower plants from inbred sunflower lines is to develop artifical culture media for callus culture and/or suspension culture (i.e., cells or small clumps of cells suspended in liquid artificial medium) of inbred sunflower lines. A further problem is to identify those inbred sunflower lines that have the potential for successful regeneration of whole plants from callus or suspension culture. The potential of any particular sunflower line to regenerate whole plants is determined by the interaction of the inherent regeneration characteristics of the sunflower line and the medium on which the regeneration of the plants is carried out. Thus, in order to readily select those inbred sunflower lines that have the potential to regenerate from tissue culture, it is desirable to develop a medium optimized for allowing regeneration from such inbred sunflower tissue culture to occur.

OBJECTS AND SUMMARY OF THE INVENTION

One of the objects of the invention is to provide a medium on which callus from inbred sunflower seed lines can regenerate sunflower plants. Another object of the invention is to provide a method for using the medium to select sunflower seed lines that can regenerate sunflower plants from callus. A further object of the invention is to provide sunflower seed plants regenerated on the medium for selecting sunflower seed lines that can regenerate from sunflower callus. A still further object of the invention is to provide a medium optimized for selecting inbred sunflower seed lines that can regenerate sunflower plants.

DETAILED DESCRIPTION OF THE INVENTION

The medium according to the instant invention is a sunflower regeneration medium suitable for selecting sunflower seed lines that are capable of regenerating sunflower plants from sunflower callus.

"Regeneration" as used herein may be defined as the formation of shoots (organogenic regeneration) or plant embryos (embryogenic regeneration) from somatic cells and the formation of an active plant from the shoots or plant embryo. Regeneration encompasses a number of stages of development. The first stage of embryogenic regeneration is the formation on the callus of small meristemic centers which resemble globular and heartshaped embryos after two weeks of dark culture on the medium. In the second stage of embryogenic regeneration and these globular and heartshaped embryos develop into small dark green spots after approximately one week of culture in daylight. These dark green spots on microscopic examination reveal torpedo shaped plant embryos having a shoot and root apex surrounded by an epidermal layer. As described further hereinbelow, these green spots may be further manipulated to produce whole sunflower plants.

According to the invention, the sunflower regeneration medium comprises a minimal salts medium, a carbohydrate source, a sunflower regeneration-effective mix of amino acids, a sunflower regeneration-effective mix of vitamins and a sunflower regeneration-effective mixture of plant hormones. As used herein the term "sunflower plant regeneration-effective" is meant to encompass media having mixes of vitamins and/or plant hormones upon which sunflower callus capable of regenerating sunflower plants, regenerates sunflower plants at a greater frequency than is observed in a sunflower growth medium that is not regeneration effective.

Sunflower regeneration effective mixes of vitamins and plant hormones have been determined for the sunflower regeneration medium according to the invention and are described presently. It should be borne in mind, however, that the sunflower regeneration-effectiveness of a particular medium is determined both by the mix and concentration of vitamins used as well as the mix and concentration of hormones used. In the examples that follow, it will be seen that by supplying plant hormones at concentrations effective for regeneration, a medium having a vitamin mix and/or concentration that is suboptimal for regeneration but growth sustaining will become regeneration effective. Thus, it has been found that a medium having White's vitamins, which are suboptimal for regeneration but growth sustaining, in addition to a mix of hormones that is regeneration effective will yield a regeneration-effective medium. It has also been demonstrated by the inventors that by supplying vitamins in a mix and concentration that is optimal for regeneration, a medium having a hormone mix and/or concentration that is suboptimal for regeneration but growth sustaining, will become regeneration-effective.

The sunflower regeneration effective medium according to the invention may be further described as a comprising a minimal salts medium suitable for the growth of plant tissue, a carbohydrate source such as sucrose, a mix of amino acids, a sunflower regeneration effective mix of vitamins, and sunflower regeneration effective mix of plant growth hormones.

Examples of minimal medium suitable for the growth of plant tissue include B5 medium (Gamborg, O. L., et al., "Nutrient Requirements of Suspension Cultures of Soybean Root Cells," *Expt'l. Cell. Res.*, 50: 151-158 (1968)); MS medium (Murashige, T. and Skoog, F (1962), *Physiologia Plantarium.*, 15: 443-97) and N6 medium (Chu, C. et al., "Establishment of an Efficient Medium for Anther Culture of Rice Through Comparative Experiments on the Nitrogen Sources," *Scientia Sinica*, 18: 659-668 (1975). White's medium is not a suitable minimal salts medium for use in the regeneration medium or methods according to the invention. (White, P. R., 1963, The Cultivation of Animal and Plant Cells, 2nd ed., Ronald Press, New York, N.Y.).

The following minimal salts are typically found in MS minimal media:
magnesium sulfate.seven hydrate ($MgSO_4.7H_2O$),
calcium chloride.dihydrate ($CaCl_2.2H_2O$),
potassium nitrate ($KNO_3$),
ammonium nitrate ($NH_4NO_3$),
potassium phosphate ($KH_2PO_4$),
manganese sulfate.four hydrate ($MnSO_4.4H_2O$),
zinc sulfate.seven hydrate ($ZnSO_4.7H_2O$),
cupric sulfate.five hydrate ($CuSO_4.5H_2O$),
cobalt chloride.six hydrate ($CoCl_2.6H_2O$ potassium iodide (KI),
boric acid (H₃BO₃),
sodium molybdinum oxide.dihydrate (Na₂MoO₄.2-H₂O),
ferrous sulfate.seven hydrate (FeSO₄.7H₂O), and
sodium ethylenediaminotetracetic acid (Na₂EDTA).

In general, as used in the invention, the exact concentration of the salts can be varied within limits without departing from the invention. To standardize the making of the media, however, the concentrations of the above listed minimal salts are as follows:

| | |
|---|---|
| MgSO₄.7H₂O | 370 milligrams/liter (mg/l) |
| CaCl₂.2H₂O | 440 mg/l |
| KNO₃ | 1900 mg/l |
| NH₄NO₃ | 1650 mg/l |
| KH₂PO₄ | 170 mg/l |
| MnSO₄.4H₂O | 22.3 mg/l |
| ZnSO₄.7H₂O | 8.6 mg/l |
| CuSO₄.5H₂O | 0.025 mg/l |
| CoCl₂.6H₂O | 0.025 mg/l |
| KI | 0.83 mg/l |
| H₃BO₃ | 6.2 mg/l |
| Na₂MoO₄.2H₂O | 0.25 mg/l |
| FeSO₄.7H₂O | 28.75 mg/l |
| Na₂EDTA | 37.25 mg/l |

In general, the sunflower regeneration effective mix of vitamins will include, nicotinic acid, pyridoxine—HCl, thiamine HCl, and glycine adenine sulfate and inositol. Within a particular concentration range, these vitamins regenerate sunflower plants at a frequency far higher than that observed in sunflower growth media having vitamin concentrations outside this particular range. A vitamin concentration of about 100–500 mg/l inositol, about 0.5 mg/l nicotinic acid, about 0.5 mg/l pyridoxine—HCl, about 1.0 mg/l thiamine—HCl, and about 2 mg/l glycine and about 40 mg/l adenine sulfate is from about 4 to about 20 times more effective in producing regeneration than the same medium having White's vitamins: 0.5 mg/l nicotinic acid; 0.1 mg/l pyridoxin.HCl; 0.1 mg/l thiamine—HCl; 1.0 mg/l Ca-pantothenate; 3.0 mg/l glycine; 1.0 mg/l cysteine; 100–500 mg/l inositol; and 40 mg/l adenine sulfate.

The regeneration medium according to the invention further includes a mix of plant hormones including at least one cytokinin such as 5-benzyladenine (BA) and at least one gibberellin such as gibberellic acid (GA₃) and at least one auxin such as naphthalene acetic acid (NAA). Concentrations exceeding 0.5 mg/l to less than 10 mg/l BA and NAA together with concentrations exceeding 0.05 to about 1.0 mg/l GA have demonstrated particular regeneration effectiveness, depending upon the light conditions used in culture.

As mentioned above, uses of the medium according to the invention include regeneration of sunflower plants from sunflower tissue in culture. The invention thus includes a method of regenerating sunflower plants from sunflower callus tissue comprising: providing a callus of sunflower tissue, growing the tissue on the sunflower regeneration medium according to the invention until greenspots form on the callus and shoots form from the greenspots.

The shoots so formed may be grafted onto sunflower seedlings using grafting techniques as described in Haberman H. H. and R. H. Wallace, *Amer. J. Bot.*, 45: 479–482 (1958). Alternatively, the callus may be transferred to a root-forming medium and grown thereon until roots form. Such root forming media are generally growth media such as MS medium or White's medium or other growth medium without hormones or with a cytokinin such as BA or with a cytokinin such as BA and gibberellin such as GA₃. To form greenspots, it is preferable to use a regeneration medium corresponding to the RM medium of Example II described hereinbelow. It is also preferable to use callus derived from hypocotyl segments of plants to be regenerated. The hypocotyl segments are taken from seedlings 3–21 days old, preferably more than 10 days old. The hypocotyl segments are grown for a period of time in complete darkness, followed by a period of daily dark and light. Preferably, the hypocotyl segments are grown on the regeneration medium in complete darkness for 1–2 weeks followed by about one week of 16 hours per day at 1000 to 3000 lux, 8 hours dark.

Once the greenspots form the callus remains on the regeneration medium for a period of time sufficient to form shoots from the greenspots, generally 2–4 weeks. Once the shoots have formed the callus may be removed to an appropriate rooting medium, preferably one with the same vitamin concentration as RM medium but which is either hormone-free or contains about 1.0 mg/l BA or about 1 mg/l BA and 0.1 mg/l GA. Plants having roots may be planted in soil to grow out, roots less shoots may be grafted to greenhouse grown seedlings according to well known procedures. (See, e.g., Habermann et al. supra.)

A further use of the medium is in a method for selecting sunflower seed lines that can regenerate or from sunflower callus. The method of selection according to the invention comprises: providing callus of sunflower tissue from a number of inbred sunflower seed lines, providing callus of sunflower tissue from a non-regenerating sunflower line as negative control and callus of sunflower tissue regenerating sunflower line as a positive control, growing the sunflower callus on the regeneration medium according to the invention for a period of time sufficient for greenspots to form on the sunflower callus, and selecting those sunflower seed lines that form greenspots from callus at a frequency greater than that of the negative control. For screening inbred sunflower lines according to the invention it is preferable to use a regeneration medium corresponding to the RM medium of Example II described hereinbelow. It is also preferable to use callus derived from hypocotyl segments of the plants to be screened. The hypocotyl segments are taken from seedlings 3–21 days old and preferably more than 10 days old. The hypocotyl segments are grown for a period of time in complete darkness followed by a period of dark and light. Preferably the hypocotyl segments are grown on the regeneration medium in complete darkness for 1–2 weeks followed by about one week of 16 hours per day at 1000–3000 lux/8 hours per day dark. Thus, the medium and method of use thereof provide a screening method for determining regenerative capacity of sunflower seed lines.

The regeneration of a sunflower plant from tissue in culture is the result of the genotype of the sunflower plant, i.e., its inherent capacity for regeneration, and the conditions under which the sunflower plant is grown, i.e., the adequacy of the medium to sustain regeneration of the sunflower plant. Thus, the ability to accurately select sunflower plants having the capacity for regeneration depends upon using a medium that has been optimized for sustaining regeneration of sunflower plants.

Using the medium described above it is possible to select sunflower lines having the capacity for regeneration by the methods described in the following examples. The following examples are intended by the inventor to be merely descriptive and non-limiting examples of the medium an uses thereof.

EXAMPLE I

*Helianthus annus* inbred line SS415B was grown aseptically. For aseptic growth the seeds were sterilized in 40% chlorine bleach with several drops of detergent for 20 minutes and rinsed with sterile water. The seed were germinated in tubes of agar media made of B5 salts (Gamborg, O. L. et al., "Nutrient Requirements of Suspension Cultures of Soybean Root Cells," *Experimental Cell Research*, 50: 148-151, 1968), 0.5% sucrose, and 0.8% agar. Explants sources were 2-3 mm hypocotyl segments from 3 to 21 day old seedling.

A sunflower regeneration medium was prepared containing minimal salts as follows:

| | | |
|---|---|---|
| $MgSO_4.7H_2O$ | 370 | milligrams/liter (mg/l) |
| $CaCl_2.2H_2O$ | 440 | mg/l |
| $KNO_3$ | 1900 | mg/l |
| $NH_4NO_3$ | 1650 | mg/l |
| $KH_2PO_4$ | 170 | mg/l |
| $MnSO_4.4H_2O$ | 22.3 | mg/l |
| $ZnSO_4.7H_2O$ | 8.6 | mg/l |
| $CuSO_4.5H_2O$ | 0.025 | mg/l |
| $CoCl_2.6H_2O$ | 0.025 | mg/l |
| KI | 0.83 | mg/l |
| $H_3BO_3$ | 6.2 | mg/l |
| $Na_2MoO_4.2H_2O$ | 0.25 | mg/l |
| $FeSO_4.7H_2O$ | 28.75 | mg/l |
| $Na_2EDTA$ | 37.25 | mg/l |

The minimal salts were supplemented with vitamins as follows:
100 or 500 mg/l inositol
0.5 mg/l nicotinic acid
0.5 mg/l pyridoxine.HCl
1.0 mg/l thiamine
2 mg/l glycine
40 mg/l adenine sulfate Amino acids were added as follows:
500 mg/l casamino acids Plant hormones were added in the concentrations listed in Table I below:

TABLE I

| | Regeneration Frequency | | | |
|---|---|---|---|---|
| Hormones | Callus Medium | | Regeneration Medium | |
| mg/L | DL | L | DL | L |
| 0.1 NAA, 0.1 BA, 0.01 $GA_3$ | 0 | 0 | 0 | 0 |
| 0.1 NAA, 0.1 BA | 0 | 0 | 0 | 0.50 |
| 1 NAA, 1 BA | 0 | 0.13 | 2.75 | 0.63 |
| 1 NAA, 1 BA 0.1 $GA_3$ | 0.50 | 0.38 | 4.25 | 0.38 |
| 0.1 2,4-D 0.1 BA, 0.01 $GA_3$ | 0.25 | 0 | 0.50 | 1.13 |
| Average | 0.15 | 0.10 | 1.50 | 0.53 |

All the media contained three percent (weight/volume) sucrose and 0.6% (weight/volume) agar. The pH was adjusted to 6.3.

A callus induction medium having the same pH, sucrose, agar and minimal salts concentration as the first medium but vitamins as follows:
100 mg/l inositol
40 mg/l thiamine
20 mg/l nicotinic acid
1 mg/l pyridoxine HCL
and the same concentrations of the hormones indicated in the Table I above was prepared.

Four 2-3 mm hypocotyl segments were placed on the two media for two weeks in complete darkness followed by one week in the light at 1000 to 3000 lux for 16 hr. light/8 hr. dark per day (DL) or for three weeks in the light (L) at 1000 to 3000 lux. Regeneration frequency, was scored as the number of shoots developing on callus per hypocotyl segment and is indicated in Table I.

The results indicate that the sunflower regeneration medium with plant hormone concentrations in the range of 1 mg/l for NAA and BA and 0.1 mg/l $GA_3$ produced a far greater amount of regeneration, than the same medium with low concentrations (0.1 mg/l NAA and BA, 0.01 mg/l $GA_3$) of the same plant hormones.

The results also indicate that the DL light regime of 2 weeks dark culture of the hypocotyl segment to produce callus, followed by 1 week of light generally yields superior shoot regeneration from sunflower callus than does the L light regime of 3 weeks culture in the light.

Furthermore, high concentration on the order of 1 mg/l of NAA and BA and 0.1 mg/l GA generally yield high regeneration of sunflower shoots from inbred sunflower callus on regeneration medium, and has a lower but significant sunflower regeneration effect on the callus medium. Low concentrations on the order of 0.1 mg/l NAA and BA and 0.01 mg/l GA, generally yield no significant inbred sunflower regeneration either on callus medium or regeneration medium.

EXAMPLE II

Seven inbred sunflower lines were tested for regeneration on the regeneration medium of Example I with 1.0 mg/l BA, 1.0 mg/l NAA and 0.1 mg/l GA (hereinafter referred to as RM) and were found to have high (inbred D and I), low (inbred A and H) and intermediate (inbred E, J, G) regeneration characteristics as determined by the numer of greenspots/callus segment under the DL light regime. The results of the test showing the regeneration of these inbreds is shown in Table II below.

TABLE II

| Inbred | Greenspots/Segment in Regeneration Medium |
|---|---|
| A | 0 |
| H | 0 |
| E | 0.1 ± 0.04 |
| J | 0.2 ± 0.1 |
| G | 1.7 ± 0.3 |
| D | 4.0 ± 0.4 |
| I | 3.7 ± 0.4 |

Using the DL regime, the same seven inbreds were then tested on five media: GT medium-disclosed as having the highest organogenesis effect in Georgievna-Todorova et al.; GT+medium—the same as GT but with 1.0 mg/l NAA, 1 mg/l BA and 0.1 mg/l GA; regeneration medium (RM); regeneration medium with 0.1 mg/l thiamine (RM 0.1); and regeneration medium (RM-) regeneration medium with 0.1 mg/l NAA, 0.1 mg/l BA and 0.01 mg/l GA. Four measures of regeneration were determined: number of inbreds regenerated; average number of greenspots regenerated/all inbreds (Avg. #GS/all); average number of greenspots regenerated/regenerating inbred (Avg. #GS/RI); and regeneration index—i.e., number of inbreds regenerated×average number of greenspots per regenerated inbred (Index). The results of the study are reported in Table III.

mix and concentration have a marked effect on regeneration of sunflower from callus.

TABLE III

| Component | Media (mg/l unless other indicated) | | | | |
|---|---|---|---|---|---|
| | GT | GT+ | RM | RM 0.1 | RM− |
| MS major | + | + | + | + | + |
| MS minor | + | + | + | + | + |
| thiamine.HCl | 0.1 | 0.1 | 1.0 | 0.1 | 1.0 |
| nicotinic acid | 0.5 | 0.5 | 0.5 | 0.5 | 0.5 |
| pyridoxine.HCl | 0.1 | 0.1 | 0.5 | 0.5 | 0.5 |
| CA-pantothenate | 1.0 | 1.0 | — | — | — |
| glycine | 3 | 3 | 2 | 2 | 2 |
| adenine sulfate | 40 | 40 | 40 | 40 | 40 |
| cysteine | 1 | 1 | — | — | — |
| inositol | 500 | 500 | 500 | 500 | 500 |
| NAA | 0.1 | 1.0 | 1.0 | 1.0 | 0.1 |
| BA | 0.1 | 1.0 | 1.0 | 1.0 | 0.1 |
| GA | 0.01 | 0.1 | 0.1 | 0.1 | 0.01 |
| Casamino acid | 500 | 500 | 500 | 500 | 500 |
| sucrose | 3% | 3% | 3% | 3% | 3% |
| agar | 0.8% | 0.8% | 0.8% | 0.6% | 0.6% |
| Inbred | Greenspots/Segment | | | | |
| A | 0 | 0 | 0 | 0 | 0 |
| H | 0 | 0 | 0 | 0 | 0.1 ± 0.1 |
| I | 0.1 ± 0.1 | 0 | 0 | 0 | 0 |
| J | 0 | 0 | 0.1 ± 0.1 | 0.1 ± 0.1 | 0 |
| G | 0 | 0.8 ± 0.3 | 0.7 ± 0.4 | 0.2 ± 0.1 | 0 |
| D | 0 | 0.5 ± 0.1 | 0.8 ± 0.2 | 0.4 ± 0.2 | 0 |
| l | 0.2 ± 0.2 | 1.7 ± 0.3 | 2.6 ± 0.6 | 4.1 ± 0.9 | 1.3 ± 0.4 |
| # Inbreds Regenerated | 2 | 3 | 4 | 4 | 2 |
| Avg GS/all | 0.04 ± 0.2 | 0.4 ± 0.08 | 0.58 ± 0.13 | 0.68 ± 0.78 | 0.19 ± 0.07 |
| Avg GS/RI | 0.15 ± 0.15 | 1.0 ± 0.23 | 1.05 ± 0.32 | 1.20 ± 0.32 | 0.70 ± 0.25 |
| Index | 0.08 ± 0.40 | 1.23 ± 0.24 | 2.32 ± 0.52 | 2.72 ± 0.72 | 0.38 ± 0.14 |

The results of these experiments clearly indicate that hormone concentration of about 1 mg/l NAA 1 mg/l BA and 0.1 mg/l GA markedly increase the regeneration effectiveness of sunflower regeneration media. Thus, GT+medium is approximately 10 times more effective in causing sunflower regeneration than GT medium as measured by the number of greenspots for all inbreds. In addition, GT+medium showed regeneration potential in three inbreds while GT showed regeneration potential in only two. Similar, results were found for RM and RM 0.1 medium.

In addition,. the experiment also shows that the vitamin mix used in RM- is far more effective in causing regeneration than the vitamin mix in GT medium.

EXAMPLE III

The effect of vitamin concentration on sunflower regeneration was tested as follows. H. annus inbred 415B was aseptically germinated and grown for 12 days in the light. 2–3 mm hypocotyl segments were obtained as in Example I.

A sunflower regeneration medium at pH 6.3, containing the minimal salts, sucrose, agar and amino acid concentrations indicated in Example I was prepared and supplemented with 1 mg/l NAA, 1 mg/l BA and 0.1 mg/l GA₃. The medium contained 0, 100, or 500 mg/l inositol and was further supplemented with vitamins in the concentrations indicated in Table III below.

Regeneration was scored as the number of greenspots developing on callus from each piece of hypocotyl segment. Four hypocotyl segments were placed on each plate and were cultured using the DL light regine. The results shown in Table IV indicate that both vitamin

TABLE IV

Regeneration (greenspots/segment)

| Vitamin mix (mg/l) | mg/l inositol | | |
|---|---|---|---|
| | 0 | 100 | 500 |
| No Vitamins (control) | 0.4 ± 0.8 | 0.2 ± 0.1 | 0.4 ± 0.2 |
| 40.0 thiamine | 3.20 ± 0.8 | 4.6 ± 0.5 | 1.9 ± 0.4 |
| 20.0 nicotinicacid 1.0 pyridoxine HCl | | | |
| 1.0 thiamine 0.5 nicotinic Acid 0.5 pyridoxine HCl | 1.3 ± 0.3 | 10.0 ± 0.9 | 8.1 ± 1.0 |
| 2.0 glycine 0.1 thiamine 0.5 nicotinic Acid 0.5 pyridoxine HCl | 1.9 ± 0.6 | 12.1 ± 1.1 | 7.5 ± 1.2 |
| 2.0 glycine 0.1 thiamine 0.5 nicotinic Acid 0.1 pyridoxine HCl 1.0 Ca-pantothenate 3.0 glycine 1.0 cysteine | 1.4 ± 0.4 | 2.6 ± 0.5 | 0.7 ± 0.2 |
| 1.0 thiamine 0.5 nicotinic Acid 0.1 pyridoxine HCl 1.0 Ca-pantothenate 3.0 glycine 1.0 cysteine | 1.6 ± 0.3 | 10.6 ± 1.2 | 10.2 ± 1.6 |

EXAMPLE IV

The effect of inositol concentration on sunflower regeneration was tested as follows. H. annus inbred 415B was aseptically germinated and grown for 12 days in the light. 2–3 mm hypocotyl segments were obtained as in Example I.

A sunflower regeneration medium at pH 6.3, containing the minimal salts, sucrose, agar, amino acid and vitamin concentrations except inositol indicated for RM medium in Example I was prepared and supplemented with 1 mg/l NAA, 1 mg/l GA and 0.1 mg/l GA$_3$. The medium contained inositol in the concentrations indicated in Table V below.

Regeneration was scored as the number of greenspots developing on callus from each piece of hypocotyl segment. Four hypocotyl segments were placed on each plate and were cultured using the DL light regime. The results shown in Table V indicate that inositol has a marked effect on regeneration of sunflower from callus in a range exceeding 1 mg/l and less than 1000 mg/l.

TABLE V

| mg/l inositol | Greenspots/hypocotyl segment |
|---|---|
| 0 | 1.0 ± 0.3 |
| 1 | 1.7 ± 0.6 |
| 5 | 3.2 ± 0.7 |
| 10 | 2.1 ± 0.5 |
| 50 | 3.3 ± 0.7 |
| 100 | 3.0 ± 0.8 |
| 500 | 3.4 ± 0.8 |
| 1000 | 1.7 ± 0.4 |

EXAMPLE V

The effect of various minimal salts media on sunflower regeneration was tested as follows. *H. annuus* inbred 415B was aseptically germinated and hypocotyl segments were obtained as in Example I.

Four minimal salts mixes corresponding to B5 salts (see Gambourg et al. hereinabove), N6 salts (see Chu et al. hereinabove), MS salts (see Murashige and Skoog hereinabove) and White's salts (see White hereinabove) were made up and were supplemented with plant hormones in the following concentrations: 1.0 mg/l BA, 1.0 mg/l NAA and 0.1 mg/l GA. The media were also supplemented with vitamins in the following concentrations: 1.0 mg/l thiamine.HCl, 0.5 mg/l nicotinic acid, 0.5 mg/l pyridoxine.HCl, 2 mg/l glycine, 50 mg/l adenine sulfate and 500 mg/l inositol. All of the media also contained 3% sucrose (wt/vol) and 0.6% agar. The hypocotyl segments were grown on the media using the DL regime. The results listed in Table VI are reported as greenspots per hypocotyl segment.

TABLE VI

| Greensports/Hypocotyl Segment | | | |
|---|---|---|---|
| White's salts | N6 salts | B5 salts | MS salts |
| 0 | 3.3 ± 0.6 | 2.2 ± 0.7 | 5.4 ± 1.0 |

EXAMPLE VI

The regeneration potential, as determined by the formation of greenspots on cultured callus; was determined for 12 production inbred lines of *H. annus*. Inbred 415B, designated Inbred I in the screening was used as a regenerating line and Inbred 89B, designated A in this screen was used as a non-regenerating control.

Seeds of each line were germinated as described in Example I. Hypocotyl segments 2-3 mm long were obtained from 12 day old seedlings. Four hypocotyl segments of each inbred were grown on each plate under the DL light regime, as described above, on a sunflower regeneration medium medium consisting of MS salts in the same concentration described in Example I, supplemented with 500 mg inositol 1.0 mg/l thiamine HCl, 0.5 mg.l nicotinic acid, 0.5 mg/l pyridoxine.HCl, 2 mg/l glycine, 40 mg/l adenine sulfate, 1 mg/l NAA, 1.0 mg/l BA, 0.1 mg/l GA, 3% (W/V) sucrose, 0.6% (W/V) agar at pH 6.3. As a control, hypocotyl segments of the same inbreds were also grown under the DL light regime on the callus induction medium described in Example I, containing 1.0 mg/l NAA and 1.0 mg/l BA at pH 6.3. The regeneration results are reported in Table VII as greenspot/per hypocotyl segment.

TABLE VII

| | Greenspots/Segment | |
|---|---|---|
| Inbred | Regeneration Medium | Callus Induction Medium |
| A | 0 | 0 |
| B | 1.8 | 0 |
| C | 0.4 | 0 |
| D | 4.0 | 0 |
| E | 0.1 | 0 |
| F | 0 | 0 |
| G | 1.7 | 0 |
| H | 0 | 0 |
| I | 3.7 | 0.1 |
| J | 0.2 | 0 |
| K | 0.3 | 0 |
| L | 0 | 0 |

The experiment shows that the regeneration medium was capable of use to distinguish sunflower lines with regeneration potential from those with little or no regeneration potential.

What is claimed is:

1. An inbred sunflower shoot or plant embryo regeneration-effective medium comprising minimal salts, Casamino acids, a carbohydrate source, an inbred sunflower shoot or plant embryo regeneration effective mixture of vitamins comprising 0.1 to less than 10 mg/l thiamine; about 0.5 mg/l nicotinic acid; 0.1 to 0.5 mg/l pyridoxine.HCl, 2 to 3 mg/l glycine, about 40 mg/l adenine sulfate and from greater than 1 mg/l to less than 1000 mg/l inositol and an inbred sunflower shoot or plant embryo regeneration effective mixture of plant hormones comprising greater than 0.5 mg/l to less than 10 mg/l benzyladenine, greater than 0.5 mg/l to less than 10 mg/l naphthalene acetic acid and greater than 0.05 mg/l to less than 1.0 mg/l gibberellic acid.

2. The regeneration-effective medium according to claim 21 wherein said concentration of said vitamins is about 1 mg/l thiamine, about 0.5 nicotinic acid, about 0.5 mg/l pyridoxine.HCl, 2 mg/l glycine and 100-500 mg/l inositol.

3. The regeneration-effective medium according to claim 2 wherein said concentration of said vitamins is about 0.1 mg/l thiamine, about 0.5 nicotinic acid, about 0.5 mg/l pyridoxine.HCl, 2 mg/l glycine and 100-500 mg/l inositol.

4. The regeneration-effective medium according to claim 3 wherein said inositol concentration is about 100 mg/l.

5. The regeneration-effective medium according to claim 3 wherein said inositol concentration is about 500 mg/l.

6. The regeneration-effective medium according to claim 1 wherein said vitamins further include greater than 0.1 mg/l and less than 10 mg/l thiamine; Ca-pantothenate and cysteine.

7. The regeneration-effective medium according to claim 6 wherein said vitamins concentration is about 1.0 mg/l thiamine, about 0.5 mg/l nicotinic acid, about 0.1 mg/l pyridoxine.HCl, about 1.0 mg/l Ca-panthothenate, about 3.0 mg/l glycine, about 1.0 mg/l cysteine and 100-500 mg/l inositol.

8. The regeneration-effective medium according to claim 7 wherein said inositol concentration is 100 mg/l.

9. The regeneration-effective medium according to claim 7 wherein said inositol concentration is about 500 mg/l.

10. The regeneration-effective medium according to claim 1 wherein said regeneration effective mixture of plant hormones comprises about 1.0 mg/l benzyladenine, about 1.0 mg/l naphthalene acetic acid and about 0.1 mg/l gibberellic acid.

11. The regeneration-effective medium according to claim 10 wherein said concentration of said vitamins is 1 mg/l thiamine, about 0.5 mg/l nicotinic acid, about 0.5 mg/l pyridoxine.HCl, 2 mg/l glycine and 100–500 mg/l inositol.

12. The regeneration-effective medium according to claim 11 wherein said concentration of said vitamins is 0.1 mg/l thiamine, about 0.5 mg/l nicotinic acid, about 0.5 mg/l pyridoxin.HCl, 2 mg/l glycine and 100–500 mg/l inositol.

13. The regeneration-effective medium according to claim 12 wherein said inositol concentration is about 100 mg/l.

14. The regeneration-effective medium according to claim 12 wherein said inositol concentration is about 500 mg/l.

15. The regeneration-effective medium according to claim 10 wherein said vitamins further include greater than 0.1 mg/l and less than 10 mg/l thiamine, Ca-pantothenate and cysteine.

16. The regeneration-effective medium according to claim 15 wherein said vitamin concentration is about 1.0 mg/l thiamine, about 0.5 mg/l nicotinic acid, about 0.2 mg/l pyridoxine.HCl, about 1.0 mg/l Ca-pantothenate, about 3.0 mg/l glycine, about 1.0 mg/l cysteine and 100–500 mg/l inositol.

17. The regeneration-effective medium according to claim 15 wherein said inositol concentration is 100 mg/l.

18. The regeneration-effective medium according to claim 15 wherein said inositol concentration is 500 mg/l.

19. A method for screening sunflower seedlines for seedlines that can regenerate shoots or plant embryos from sunflower callus comprising the steps of:
providing sunflower callus from a number of inbred sunflower seedlines to be screened;
providing callus of a non-regenerating sunflower line as a negative control;
providing callus of a shoot or plant embryo regenerating sunflower line as a positive control;
growing the sunflower callus on a sunflower shoot or plant embryo regeneration effective medium comprising minimal salts, Casamino acids, carbohydrate source, a shoot or plant embryo regeneration effective mixture of vitamins comprising 0.1 to less than 10 mg/l thiamine; about 0.5 mg/l nicotinic acid; 0.1 to 0.5 mg/l pyridoxine.HCl; 2 to 3 mg/l glycine, about 40 mg/l adenine sulfate and from greater than 1 mg/l to less than 1000 mg/l inositol and a sunflower shoot or plant embryo regeneration effective mixture of plant hormones comprising greater than 0.5 mg/l to less than 10 mg/l benzyladenine, greater than 0.5 mg/l to less than 10 mg/l napthalene acetic acid and greater than 0.05 mg/l to less than 1.0 mg/l gibberellic acid for a period of time sufficient for greenspots to form on said sunflower callus; and
selecting those sunflower seedlines that form greenspots at a frequency greater than that of said negative control.

20. A method for screening sunflower seedlines for seedlines that can regenerate shoots or plant embryos from sunflower callus comprising the steps of:
providing sunflower callus from a number of inbred sunflower seedlines to be screened;
providing callus of a non-regenerating sunflower shoot or plant embryo line as a negative control;
growing the sunflower callus on a sunflower regeneration effective medium comprising minimal salts, Casamino acids, carbohydrate source, a sunflower shoot or plant embryo regeneration-effective mixture of vitamins comprising 0.1 to less than 10 mg/l thiamine; about 0.5 mg/l nicotinic acid; 0.1 to 0.5 mg/l pyridoxine.HCl, 2 to 3 mg/l glycine, about 40 mg/l adenine sulfate and from greater than 1 mg/l to less than 1000 mg/l inositol and a sunflower shoot or plant embryo regeneration effective mixture of plant hormones comprising greater than 0.5 mg/l to less than 10 mg/l benzyladenine, greater than 0.5 mg/l to less than 10 mg/l naphthalene acetic acid and greater than 0.05 mg/l to less than 1.0 mg/l gibberellic acid for a period of time sufficient for greenspots to form on said sunflower callus; and
selecting those sunflower seedlines that form greenspots at a frequency greater than that of said negative control.

21. A method of regenerating sunflower shoots and plant embryos from sunflower callus comprising
providing a callus of sunflower tissue;
growing said callus on a sunflower shoot and plant embryo regeneration-effective medium comprising minimal salts, Casamino acids, carbohydrate source, a sunflower shoot and plant embryo regeneration-effective mixture of vitamins comprising 0.1 to less than 10 mg/l thiamine; about 0.5 mg/l nicotinic acid, 0.1 to 0.5 mg/l pyridixone.HCl, 2 to 3 mg/l glycine, about 40 mg/l adenine sulfate and from greater than 1 mg/l to less than 1000 mg/l inositol and a sunflower shoot and plant embryo regeneration effective mixture of plant hormones comprising greater than 0.5 mg/l to less than 10 mg/l benzyladenine, greater than 0.5 mg/l to less than 10 mg/l naphthalene acetic acid and greater than 0.5 mg/l to less than 1.0 mg/l gibberellic acid until greenspots form on said callus, and allowing shoots to grow from said greenspots.

* * * * *